United States Patent
Talgorn et al.

(10) Patent No.: US 12,138,117 B2
(45) Date of Patent: Nov. 12, 2024

(54) ONE-DIMENSIONAL POSITION INDICATOR

(71) Applicant: KONINKLIJKE PHILIPS N.V., Eindhoven (NL)

(72) Inventors: Elise Claude Valentine Talgorn, Eindhoven (NL); Monique Hendriks, Eindhoven (NL); Tomq Djajadiningrat, Utrecht (NL); Niels Laute, Venlo (NL); Jaap Knoester, Utrecht (NL); Hyelin Lee, Amsterdam (NL); Reinoud Bosman, Amsterdam (NL)

(73) Assignee: Koninklijke Philips N.V., Eindhoven (NL)

( * ) Notice: Subject to any disclaimer, the term of this patent is extended or adjusted under 35 U.S.C. 154(b) by 120 days.

(21) Appl. No.: 18/015,814

(22) PCT Filed: Jul. 7, 2021

(86) PCT No.: PCT/EP2021/068727
§ 371 (c)(1),
(2) Date: Jan. 12, 2023

(87) PCT Pub. No.: WO2022/013022
PCT Pub. Date: Jan. 20, 2022

(65) Prior Publication Data
US 2023/0255590 A1    Aug. 17, 2023

(30) Foreign Application Priority Data

Jul. 14, 2020 (EP) ..................... 20185638

(51) Int. Cl.
*A61B 8/00* (2006.01)
*A61B 6/00* (2006.01)
(Continued)

(52) U.S. Cl.
CPC ............ *A61B 8/4263* (2013.01); *A61B 6/461* (2013.01); *A61B 6/547* (2013.01); *A61B 8/461* (2013.01);
(Continued)

(58) Field of Classification Search
CPC ............ G06T 7/70; G06T 2207/30004; G09B 23/286; A61B 8/4263; A61B 8/461;
(Continued)

(56) References Cited

U.S. PATENT DOCUMENTS 6,937,696 B1   8/2005 Mostafavi
2014/0004488 A1   1/2014 Tepper et al.
(Continued)

OTHER PUBLICATIONS

International Search Report and Written Opinion From PCT/EP2021/068727 Mailed Sep. 17, 2021.

*Primary Examiner* — Boniface N Nganga

(57) ABSTRACT

Disclosed herein is a medical system (100, 300, 500) comprising: a memory (110) storing machine executable instructions, at least one set of predetermined coordinates (124), and a position identifying algorithm (122). The position identifying algorithm is configured for outputting a set of current coordinates (128) for each of the at least one set of predetermined coordinates in response to receiving a current image descriptive of an object (306, 310). The execution of machine executable instructions (120) causes a computational system (104) to repeatedly receive (200) a current image (126) from a camera system (304). The execution of machine executable instructions (120) causes a computational system (104) to perform the following for the current image: receive (202) the set of current coordinates for each of the at least one set of predetermined coordinates in response to inputting the current image into the position identifying algorithm; calculate (204) a positional difference (130) between the at least one set of predetermined coordi-
(Continued)

nates and its set of current coordinates; calculate (206) a one-dimensional value (134) from positional difference using an objective function; and provide (208) a one-dimensional position indicator (136, 314, 600, 602, 608, 800, 900, 1002) for each of and controlled by each one-dimensional value in real time using a user interface (108, 308, 416, 418).

13 Claims, 14 Drawing Sheets

(51) Int. Cl.
*A61B 6/46* (2024.01)
*G06T 7/70* (2017.01)
(52) U.S. Cl.
CPC ...... *G06T 7/70* (2017.01); *G06T 2207/30004* (2013.01)
(58) Field of Classification Search
CPC .. A61B 8/46; A61B 8/58; A61B 6/461; A61B 6/547
See application file for complete search history.

(56) References Cited

U.S. PATENT DOCUMENTS

| | | |
|---|---|---|
| 2015/0020898 A1 | 1/2015 | Tseng |
| 2015/0208981 A1 | 7/2015 | Oh et al. |
| 2018/0247427 A1 | 8/2018 | Geiger et al. |
| 2020/0135055 A1 | 4/2020 | Buras et al. |

ONE-DIMENSIONAL POSITION INDICATOR

CROSS REFERENCE TO RELATED APPLICATIONS

This application is a U.S. national phase application of International Application No. PCT/EP2021/068727 filed Jul. 7, 2021, which claims the benefit of EP Application Serial No. 20185638.2 filed Jul. 14, 2020 and is incorporated herein by reference.

FIELD OF THE INVENTION

The invention relates to medical imaging, in particular to the positioning of objects for medical imaging.

BACKGROUND OF THE INVENTION

Various medical imaging modalities such as X-ray, fluoroscopy, Magnetic Resonance Imaging (MRI), Computed Tomography, Positron Emission Tomography, and Single Photon Emission Tomography enable detailed visualization of anatomical structure of a subject. A common feature of all of these imaging modalities is that they involve the proper placement of a object. The object could, for example be an ultrasound transducer or the subject being imaged.

United States patent application publication US20140004488 A1 discloses a system for training practitioners in use of an ultrasound system including a unit for managing workflow of an ultrasound training session, a user interface for providing ultrasound training session instructions to a practitioner operating an ultrasound machine and for receiving input from a trainee, a unit for communication with the ultrasound machine, for collecting one or more ultrasound images produced during the training session from the ultrasound machine, a unit for image processing the ultrasound images, and a unit for assessing quality of the ultrasound images. A method for monitoring practitioner proficiency in use of an ultrasound system including providing the practitioner with an ultrasound task definition, collecting one or more ultrasound images produced by the practitioner during performance of the ultrasound task from an ultrasound machine, image processing the ultrasound images, and assessing quality of the ultrasound images. Related apparatus and methods are also described.

SUMMARY OF THE INVENTION

The invention provides for a medical system, a method, and a computer program in the independent claims. Embodiments are given in the dependent claims.

A difficulty in performing medical imaging is that it may require the precise placement of equipment and/or a subject. This typically requires an operator to undergo extensive training and to practice. Embodiments may provide for a medical system that enables the precise placement of objects for medical imaging with a minimal amount of training.

This may be achieved by repeatedly receiving a current image from a camera system. The current image is then input into a position identifying algorithm that provides current coordinates of the object. The current coordinates are then compared to predetermined coordinates, which results in the calculation of a position difference. The positional difference is the difference in the coordinates. This positional difference may be multi-dimensional coordinates. The positional difference is then input into an objective function that outputs a one-dimensional value. The one-dimensional value is then used to control a one-dimensional position indicator.

The one-dimensional position indicator may then be provided to an operator of a medical system or a subject being imaged. The complex alignment or position of an object or subject is reduced to the one-dimensional value which controls the one-dimensional position indicator. As a subject or operator moves to a worse position the value of the one-dimensional position indicator changes. Experimentation by the operator or the subject with small motions quickly establishes how the object or subject should be moved.

The objective function may be any type of objective function which can turn a multi-dimensional positional difference to a one-dimensional value. The objective function may take different forms similar in the way in which objective functions can be used by optimization problems used in numerical methods.

In one aspect the invention provides for a medical system. The medical system comprises a memory storing machine-executable instructions, at least one set of predetermined coordinates, and a position identifying algorithm. The position identifying algorithm is configured for outputting a set of current coordinates for each of the at least one set of predetermined coordinates in response to receiving a current image descriptive of an object. The position identifying algorithm may for example be an image segmentation algorithm. Various ways of implementing a segmentation algorithm or a position identifying algorithm exist. For example, the image may be registered to an anatomical atlas. In other examples the position identifying algorithm could be a template or a model-based matching system. In yet other examples the position identifying algorithm could be implemented for example as a trained neural network.

The medical system further comprises a computational system configured for controlling the medical system. Execution of the machine-executable instructions causes the computational system to repeatedly receive the current image from a camera system. For example, the current image may be received in the form of a video stream or sequence of current images. Execution of the machine-executable instructions further causes the computational system to perform the following for the current image: this is to receive the set of current coordinates for each of the at least one set of predetermined coordinates in response to inputting the current image into the position identifying algorithm. Execution of the machine-executable instructions further causes the computational system to perform the following for the current image and this is to calculate a positional difference between the at least one set of predetermined coordinates and its set of current coordinates.

In other words, for each of the at least one set of predetermined coordinates there is a positional difference which is calculated. For the current image execution of the machine-executable instructions further causes the computational system to calculate a one-dimensional value for each of the at least one set of predetermined coordinates by inputting the positional difference for each of the at least one set of predetermined coordinates into an objective function. In performing numerical optimizations, a number of values are typically input into an objective function and then this objective function is either maximized or minimized. In numerical methods the objective function is then used to search for an optimal value. In this case, the objective function is used to provide an easy means for a subject to understand how to properly position the object. For the current image, execution of the machine-executable instructions further causes the computational system to provide a one-dimensional position indicator for each of and controlled by each one-dimensional value in real time using a user interface.

Instead of displaying complex diagrams illustrating the proper positioning of the object, the one-dimensional position indicators are used. People who have been highly trained or have a very good sense of spatial thinking may be able to look at complicated diagrams or instructions and understand how to move the object or themselves to properly position the object. However, in many situations it is not possible to train people to do this. If the positioning involves complex body part motions, people might not have the body awareness needed to reproduce the spatial instructions with their body, rendering them unable to follow the instructions.

The one-dimensional position indicator provides feedback if the object has the proper position. The person trying to position the object can receive a stimulus from the one-dimensional position indicator from the user interface and from its one-dimensional change understand without any training if the object is getting closer or further away from being in the proper position.

The at least one set of predetermined coordinates may in some instances just be a single set of predetermined coordinates. This for example may be useful in positioning a rigid object. In other cases, such as when the object is a subject or patient, the coordinates may be connected by elastic or moveable parts or components. One particular example, which will be discussed later, is the positioning of two shoulder joints. A subject can move these independently. To provide for proper position of both, in this case two one-dimensional position indicators are provided. For more complicated objects and positioning any number of one-dimensional position indicators can be provided.

The camera system may take different forms in different examples. For example, it could be a stereo camera. In other examples it may be multiple cameras. These may for example be useful for generating a three-dimensional image. In another example the camera may be a three-dimensional camera such as a time-of-flight camera.

In another embodiment the one-dimensional position indicator for each of the at least one set of predetermined coordinates is adapted to provide real time feedback on the alignment of the object to the at least one set of predetermined object coordinates. As was mentioned above, the use of the one-dimensional position indicators may provide a means of achieving this with minimal or zero training.

In another embodiment the at least one set of predetermined coordinates is a single set of predetermined coordinates. The object is an ultrasound transducer. The single set of predetermined coordinates is an orientation and placement of the ultrasound transducer on a subject.

For example, the position identifying algorithm may also be used to identify a position of the subject. The at least one set of predetermined coordinates may be referenced to a location on the subject. The one-dimensional position indicator may then be used to guide the operator of the ultrasound transducer to the proper position. This may be useful for training operators of ultrasound transducers as well as providing a system which is useable by physicians or medical technicians who have a minimal amount of training in using a diagnostic ultrasound system.

In another embodiment the at least one set of predetermined coordinates are anatomical locations. In this case the object is a subject or patient. This embodiment may be particularly beneficial because various parts of the patient or subject are flexible and may be moved relatively independently. To perform a complicated medical examination or diagnostic medical imaging procedure it is often necessary to place multiple portions or parts of the subject's body in the proper position. The one-dimensional position indicator can be displayed to the subject to provide a means to aid them in positioning themselves correctly.

In another embodiment the medical system further comprises the camera system and the display.

In another embodiment the medical system further comprises a medical imaging system. Each of the at least one set of predetermined coordinates defines a three-dimensional position and orientation of a body part of the subject relative to an imaging zone of the medical imaging system. The medical imaging zone may be a region of space where medical imaging data that is descriptive of the body of the subject may be acquired. This may for example be within the imaging zone of a magnetic resonance imaging system or within the path of an X-ray beam for a digital X-ray or fluoroscope system. In some instances, the display is configured for providing feedback to the subject. The display may be used for providing the one-dimensional position indicator for each of the one-dimensional value in real time to the subject.

In another embodiment the medical imaging system is a magnetic resonance imaging system.

In another embodiment the medical imaging system is a diagnostic ultrasound system.

In another embodiment the medical imaging system is a computed tomography system.

In another embodiment the medical imaging system is a positron emission tomography system.

In another embodiment the medical imaging system is a single photon emission tomography system.

In another embodiment execution of the machine-executable instructions further causes the computational system to receive an imaging protocol selection. For example, a physician may order that particular diagnostic radiological procedure is to be performed. This may for example be a particular type of X-ray or magnetic resonance imaging protocol on a particular anatomical region of the subject. The imaging protocol selection may identify the positioning that the subject should be put into for a particular imaging procedure.

Execution of the machine-executable instructions further causes the computational system to retrieve a set of positioning instruction steps for positioning the subject by querying a database with the imaging protocol selection. The set of positioning instruction steps describe a sequence of positioning instructions. At least one of the sequence of positioning instructions comprises the at least one set of predetermined coordinates. In this step the positioning instruction steps are a set of steps which may be used to place the subject in the proper positioning for the particular medical imaging protocol.

At least one of these steps uses the one-dimensional position indicator. Execution of the machine-executable instructions further causes the computational system to provide the predefined sequence of positioning instructions using the user interface. Often times the user interface will have a display which is then presented to the subject optically. However, there are other alternatives. For example, the user interface may provide auditory or haptic instructions for subjects who are visually impaired. This may for example include a description of how the subject should position their body and then uses the one-dimensional position indicators so that the subject is able to position her or himself without feedback.

Execution of the machine-executable instructions further causes the computational system to monitor subject motion during displaying the predetermined sequence of positioning instructions. The position indicator is provided in real time for the at least one of the predefined sequence of positioning instructions. This embodiment may be beneficial because it may provide a complete system which may enable a subject to position themselves into difficult or complicated poses for medical imaging. As was mentioned above, some embodiments may also provide a means for visually impaired subjects to perform this also.

In another embodiment, execution of the machine executable instructions are configured to cause the computational system to provide the one-dimensional position indicator in real time after the subject motion is descriptive of a failure to successfully complete the at least one of the predefined sequence of positioning instructions. When the predefined sequence of positioning instructions is provided, the subject motion may be monitored to check if the subject is positioning her or his self properly. If the system detects that the subject is not correctly positioned or is unable to attain a correct position or posture within a predetermined time limit the system may then automatically display one or more one-dimensional position indicators to assist the subject.

In another embodiment execution of the machine-executable instructions further causes the computational system to provide a success indicator indicating positioning after each of the predefined sequence of positioning instructions if the set of current conditions satisfy a predefined criterion. For example, if the current coordinates are within a predetermined distance or positional difference from the predetermined coordinates then the system may accept the subject as having been correctly positioned. The success indicator may for example be a particular sound or audible indicator or it may also be an object or symbol which is displayed on a display so the subject knows that this particular positioning has been achieved. Execution of the machine-executable instructions further causes the computational system to remove a success indicator if a set of current coordinates no longer satisfies the predetermined criterion. In positioning for some radiological procedures, the subject may need to be sequentially positioned in a number of different positions to attain a final pose which is used for the medical imaging procedure. It may be difficult for the subject to maintain a position achieved in a prior movement. The success indicator may be used to provide feedback to the subject to indicate if the new motion has inadvertently caused the subject to lose positioning caused by a prior movement.

In another embodiment each of the at least one set of predetermined coordinates defines a three-dimensional position and orientation of a body part of the subject. As was mentioned above, various body parts of the subject may be connected elastically or in a flexible or moveable way. A good example is the positioning of two shoulders in front of an X-ray plate. The subject is able to move each shoulder relatively independently. In this case, two one-dimensional position indicators will be provided, one for each shoulder.

In another embodiment the user interface is configured to provide at least one of the one-dimensional position indicator for each of the at least one set of predetermined coordinates as a haptic signal. The type of stimulus or feedback that is provided to a subject may take different forms. It may for example be provided visually, via audio information or also as a haptic signal. If there are multiple one-dimensional position indicators the different types of stimulus can be mixed.

In another embodiment the user interface is configured to provide at least one of the one-dimensional position indicator for each of the at least one set of predetermined coordinates as an audio signal. This embodiment may be particularly beneficial to subjects who are visually impaired. The one-dimensional position indicator may be provided in a variety of different ways. For example, an individual one-dimensional position indicator may be used to vary the pitch of a tone, it may be used to vary the timbre of a tone, it may be used to vary the loudness of a tone and it may also be used to modify the stereo position of the sound. The stereo position of the sound may be for example varied by panning the relative volumes to the left or the right ear of the subject. Subjects also have a fairly highly developed sense of spatial location of sounds from various psychoacoustic effects. For example, in addition to varying the relative loudness of the sound or tone, there may be slight delays which are introduced to form a very accurate spatial stereo image in the mind of the subject. These various audio signals could also be combined to convey to a subject more than one one-dimensional position indicator. For example, if there are two one-dimensional position indicators one could be used to vary the pitch or timbre of a tone and the other could be used to vary the stereo location of the sound, as was described above, using the psychoacoustic effects or the relative volume. This means that even a visually impaired person would then have the ability to position themselves into a highly complex position for a medical imaging procedure with a minimal amount of assistance.

In another embodiment the audio signal comprises an amplitude change.

In another embodiment the audio signal comprises a pitch change.

In another embodiment the audio signal comprises a timbre change.

In another embodiment the audio signal comprises a change in a stereo audio location or a position in a stereo audio field, as it is sometimes described.

In another embodiment the user interface is configured to provide at least one of the one-dimensional position indicator for each of the at least one set of predetermined coordinates as a visual position indicator on a display. This may be beneficial because a display may be used for displaying a large number of the one-dimensional position indicators. The display may also be used for providing other information such as written instructions or a graphic which provides an additional guidance to the subject.

In another embodiment the visual position indicator is an object location along a predetermined path. For example, an object can be moved along a path away from a resting point. When the resting point is reached then the predetermined coordinates and the current coordinates may agree within a predetermined amount.

In another embodiment the visual position indicator is provided as a rotational position on a display. As with the predetermined path, a particular rotational position may correspond to the predetermined coordinates and the current coordinates being aligned within a predetermined amount.

In another embodiment the visual position indicator is provided as an object size. For example, the object size could be increased or decreased and a particular size may correspond to the predetermined coordinates and the current coordinates being aligned within the predetermined amount.

In another embodiment the visual position indicator is provided as a color change of a displayed object or region. For example, the color could be changed or morphed as the predetermined coordinates and the current coordinates become aligned within the predetermined amount. A concrete example would be a color change from red to green indicating proper positioning.

In another embodiment the position identifying algorithm is configured to output a set of current coordinates using a template-based matching algorithm. This may also be referred to as a model-based matching algorithm.

In another embodiment the position identifying algorithm is configured to output the set of current coordinates using a pictorial structural model with a joint likelihood maximization algorithm.

In another embodiment the position identifying algorithm is configured to output the set of current coordinates using a trained neural network.

In another embodiment the position identifying algorithm is configured to output the set of current coordinates using a probabilistic boosting tree algorithm.

In another embodiment the position identifying algorithm is configured to output the set of current coordinates using a deformable model.

In another embodiment the objective function is a linear combination of coordinates making up the positional difference.

In another embodiment the objective function is a root mean square (RMS) value of coordinates making up the positional difference.

In another embodiment the objective function is a linear combination of the absolute value of the coordinates making up the positional difference.

In another embodiment the objective function is a weighted linear combination of the absolute value of the coordinates making up the positional difference.

In another embodiment the objective function is a norm of coordinates making up the positional difference.

In another embodiment the objective function is an L2 norm of coordinates making up the positional difference.

In another aspect the invention provides for a method of operating a medical system. The method comprises repeatedly receiving an image from a camera system. The method further comprises receiving for the current image the set of current coordinates for each of the at least one set of predetermined coordinates in response to inputting the current image into a position identifying algorithm. The position identifying algorithm is configured for outputting a set of current coordinates for each of the at least one set of predetermined coordinates in response to receiving a current image descriptive of an object. The method further comprises calculating for the current image a positional difference between the at least one set of predetermined coordinates and its set of current coordinates. The method further comprises calculating for the current image a one-dimensional value for each of the at least one set of predetermined coordinates by inputting the positional difference for each of the at least one set of predetermined coordinates into an objective function. The method further comprises providing for the current image a one-dimensional position indicator for each of and controlled by each one-dimensional value in real time using a user interface. The advantages of this embodiment have been previously discussed.

In another aspect the invention provides for a computer program comprising machine-executable instructions for execution by a computational system controlling a medical system. The computer program further comprises a position identifying algorithm or an implementation of the position identifying algorithm. The position identifying algorithm is configured for outputting a set of current coordinates for each of the at least one set of predetermined coordinates in response to receiving a current image descriptive of an object. Execution of the machine-executable instructions causes the computational system to repeatedly receive a current image from a camera system.

Execution of the machine-executable instructions further causes the computational system to receive for the current image the set of current coordinates for each of the at least one set of predetermined coordinates in response to inputting the current image into the position identifying algorithm. Execution of the machine-executable instructions further causes the computational system to calculate for the current image a positional difference between the at least one set of predetermined coordinates and its set of current coordinates.

Execution of the machine-executable instructions further causes the computational system to calculate for the current image a one-dimensional value for each of the at least one set of predetermined coordinates by inputting the positional difference for each of the at least one set of predetermined coordinates into an objective function. Execution of the machine-executable instructions further causes the computational system to provide for the current image a one-dimensional position indicator for each of and controlled by each one-dimensional value in real time using a user interface. The advantages of this embodiment have been previously discussed.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor or computational system of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the computational system of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the computational system. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a computational system. 'Computer storage' or 'storage' is a further example of a computer-readable storage medium. Computer storage is any non-volatile computer-readable storage medium. In some embodiments computer storage may also be computer memory or vice versa.

A 'computational system' as used herein encompasses an electronic component which is able to execute a program or machine executable instruction or computer executable code. References to the computational system comprising the example of "a computational system" should be interpreted as possibly containing more than one computational system or processing core. The computational system may for instance be a multi-core processor. A computational system may also refer to a collection of computational systems within a single computer system or distributed amongst multiple computer systems. The term computational system should also be interpreted to possibly refer to a collection or network of computing devices each comprising a processor or computational systems. The machine executable code or instructions may be executed by multiple computational systems or processors that may be within the same computing device or which may even be distributed across multiple computing devices.

Machine executable instructions or computer executable code may comprise instructions or a program which causes a processor or other computational system to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly. In other instances, the machine executable instructions or computer executable code may be in the form of programming for programmable logic gate arrays.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a computational system of a general purpose computer, special purpose computer, or other programmable data processing apparatus to produce a machine, such that the instructions, which execute via the computational system of the computer or other programmable data processing apparatus, create means for implementing the functions/acts specified in the flowchart and/or block diagram block or blocks.

These machine executable instructions or computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The machine executable instructions or computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer to indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator. A user interface may also provide audio or haptic information to a user or operator.

A 'hardware interface' as used herein encompasses an interface which enables the computational system of a computer system to interact with and/or control an external computing device and/or apparatus. A hardware interface may allow a computational system to send control signals or instructions to an external computing device and/or apparatus. A hardware interface may also enable a computational system to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Medical imaging data is defined herein as being recorded measurements made by a tomographic medical imaging system descriptive of a subject. The medical imaging data may be reconstructed into a medical image. A medical image id defined herein as being the reconstructed two- or three-dimensional visualization of anatomic data contained within the medical imaging data. This visualization can be performed using a computer.

BRIEF DESCRIPTION OF THE DRAWINGS

In the following preferred embodiments of the invention will be described, by way of example only, and with reference to the drawings in which.

DETAILED DESCRIPTION OF EMBODIMENTS

Like numbered elements in these figures are either equivalent elements or perform the same function. Elements which have been discussed previously will not necessarily be discussed in later figures if the function is equivalent.

Figure 1:
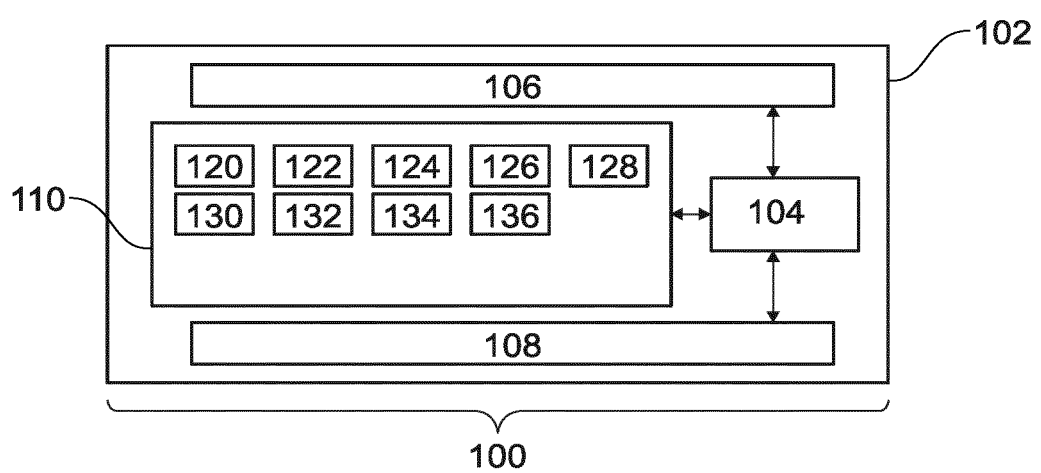
FIG. 1 illustrates an example of a medical system.

FIG. 1 illustrates an example of a medical system 100. The medical system 100 in FIG. 1 is shown as comprising a computer system 102. The computer system 102 could represent one or more computer systems in a particular location or may be distributed for example across the internet or as a web service. The computer system 102 is shown as comprising a computational system 104. The computational system 104 may for example be one or more processing cores that are located at one or more different locations. The computational system 104 is shown as being connected to an optional hardware interface 106. The hardware interface 106 may for example be used for controlling other components of the medical system 100 if they are present. The computational system 104 is further shown as comprising an optional user interface 108. The user interface 108 may for example be useful for providing optical, audio or haptic feedback to an operator or subject. The computational system 104 is further shown as being connected to a memory 110. The memory 110 is intended to represent any combination of memories or memory which is accessible to the computational system 104. This may include such things as hard drives, SSDs, or even external memory on optical media or across a network.

The memory 110 is shown as containing machine-executable instructions 120. The machine-executable instructions 120 may enable the computational system 104 to provide various data processing and image processing tasks as well as controlling other components of the medical system 100. The memory 110 is further shown as containing a position identifying algorithm 122. The position identifying algorithm 122 is configured for receiving a current image 126 and outputting at least one set of current coordinates 128. The memory 110 is further shown as containing at least one set of predetermined coordinates 124. The memory 110 is shown as containing the current image 126. The memory 110 is further shown as containing the set of current coordinates for each of the at least one set of predetermined coordinates that were received by inputting the current image 126 into the position identifying algorithm 122.

The memory is further shown as containing a positional difference 130 for each of the at least one set of predetermined coordinates 124. This is calculated by calculating a difference in the coordinates between each of the at least one set of predetermined coordinates 124 and its corresponding set of current coordinates 128. The memory 110 is further shown as containing an objective function 132. The objective function 132 takes a positional difference 130 as input and then outputs a one-dimensional value 134. The objective function 132 can take different forms in different examples; however, for example it could be simply the mean square of the difference between the coordinates, in other examples various coordinates may have different weighting functions so that if a particular coordinate is more important in positioning the object.

The memory 110 is further shown as containing a copy of the one-dimensional values 134. The one-dimensional values 134 are then used for controlling one-dimensional position indicators 136. The one-dimensional position indicators 136 may for example be rendered or provided using the user interface 108 or provided to a different computer or computational system to provide these.

Figure 2:
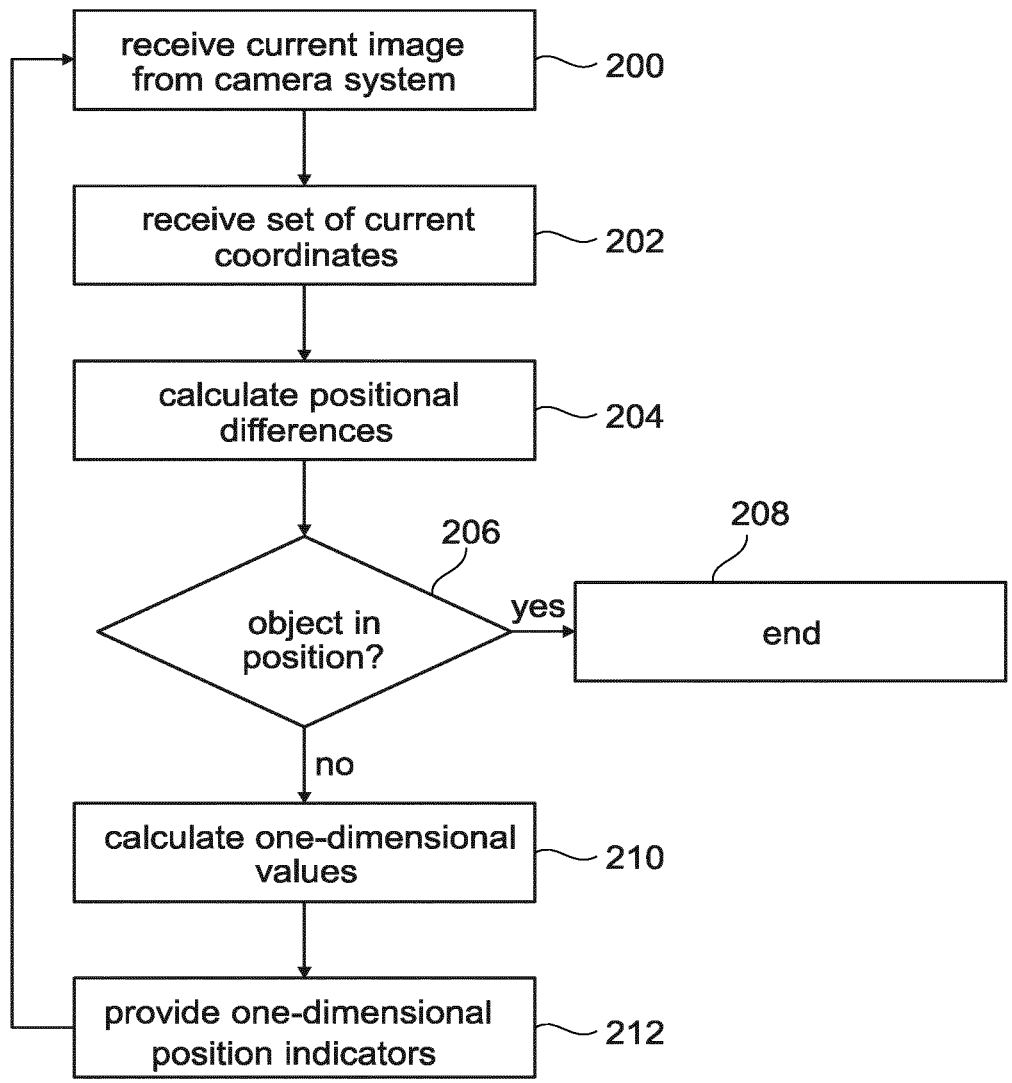
FIG. 2 shows a flow chart which illustrates a method of using the medical system of FIG. 1.

FIG. 2 shows a flowchart which illustrates a method of operating the medical system 100 of FIG. 1. First, in step 200, the current image 126 is received from a camera system. Next, in step 202, the set of current coordinates 128 is received by inputting the current image 126 into the position identifying algorithm 122. Next, in step 204, the positional difference 130 between the set of current coordinates 128 and the set of predetermined coordinates 124 is calculated.

The method then proceeds to an optional decision box 206. In box 206 the question 'is the object in position?' is asked. For example, a predetermined criterion could be used to determine if the positional difference 130 is small enough that it indicates that the object has been correctly positioned. If the answer to the question in box 206 is yes, then the method proceeds optionally to step 208, which is to end the method. If the answer to the question in box 206 is no, which means that the object has not been correctly positioned, the method proceeds to step 210. In step 210, the one-dimensional values 134 are calculated by inputting the positional difference 130 into the objective function 132.

After step 210 is performed, the method proceeds to step 212. In step 212 the one-dimensional position indicator 136 is provided. The one-dimensional values 134 are used to control the one-dimensional position indicators 136. As was mentioned, the various one-dimensional position indicators could be provided using a combination of haptic, visual, or audio signals. After step 212 the method returns to step 200. In this example the method provides a closed control loop.

Figure 3:
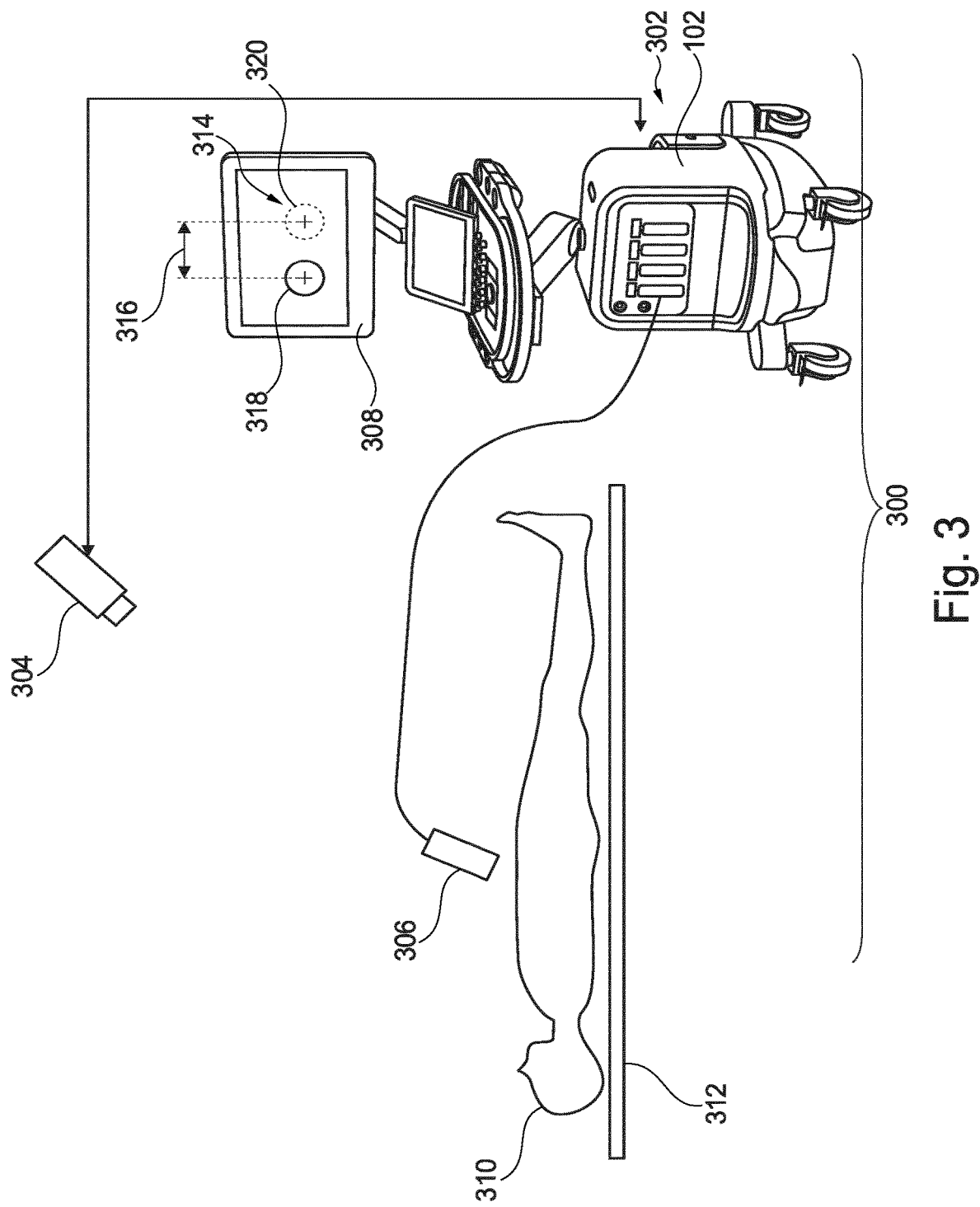
FIG. 3 illustrates a further example of a medical system.

FIG. 3 illustrates a further example of a medical instrument 300. The medical instrument 300 is similar to the medical instrument 100 in FIG. 1 except that it additionally comprises a diagnostic ultrasound system 302. The diagnostic ultrasound system 302 is further shown as comprising a camera system 304 for acquiring the current image. The diagnostic ultrasound system 302 is further shown as comprising an ultrasound transducer 306 and a display 308. A computer system 102, such as is illustrated in FIG. 1, is also shown as being integrated into the diagnostic ultrasound system 302. On a subject support 312 there is a subject 310 that is reposing. The ultrasound transducer 306 may be moved manually to the subject 310 to perform an examination. The camera system 304 acquires the current image repeatedly. The position identifying algorithm may for example be able to identify the location of the ultrasound transducer 306 relative to the anatomy of the subject 310.

On the display 308 is shown as single one-dimensional position indicator 314. The ultrasound transducer 306 may be aligned in terms of rotation, pressure, and angle with respect to the subject 310. However, in this example there is only a single one-dimensional position indicator 314. The objective function 132 is used to reduce the alignment to a one-dimensional displacement 316 between an object 318 that is displayed on the display 308 and a position of the object when the transducer is aligned 320. As the ultrasound transducer 306 is more poorly aligned the one-dimensional displacement 316 decreases. By watching the single one-dimensional position indicator 314, the operator can eventually correctly position the ultrasound transducer 306 in the right position to perform an examination. This may enable people with a minimal amount of training to correctly operate the diagnostic ultrasound system 302.

Examples may also be used for position ultrasound transducers. Ultrasound is not a push-button technique. It requires an expert operator (the time to acquire the right maneuverability skills and perform good cardiac examinations can take up to 2 years) to acquire a good ultrasound image, meaning the repeatability and reproducibility of a given image is limited by its complexity. The complexity arises due to the localization step requiring the sonographer to move the probe on the patient's body to reach the target location with the correct probe orientation while mentally integrating multiple images from the real-time ultrasound stream to reconstruct the patient's anatomy.

The main goal of the ultrasound examination is obtaining accurate photos of the region of interest inside the patient. For this, fine movements with the probe are needed to get to the right view of the internal organ. Such movements include:

Putting fine pressure with the probe on the skin
Rotating to X°
Rolling the probe The achieved image quality is highly sensitive to the probe location and orientation, as well as to external, subject-dependent factors, including for instance the subject's position and breathing phase. Thus, the overall quality of an ultrasound exam heavily relies on the expertise and experience of the sonographer performing the examination. It may take some time for a less experienced sonographer to move the probe on the subject's body to obtain the desired image plane. The dependency on the sonographer is one of the main sources of variations for establishing accurate quantitative ultrasound diagnoses. The dependency is particularly detrimental to the reproducibility of follow-up ultrasound examinations (examinations that are performed after an initial examination), making comparisons difficult.

Examples may provide for the guidance of ultrasound probes or transducers and can therefore enable less-experienced users to perform high-quality and fast ultrasound examination. This can be a disruptor e.g. in emergency care, and delocalized care in general.

Figure 4:
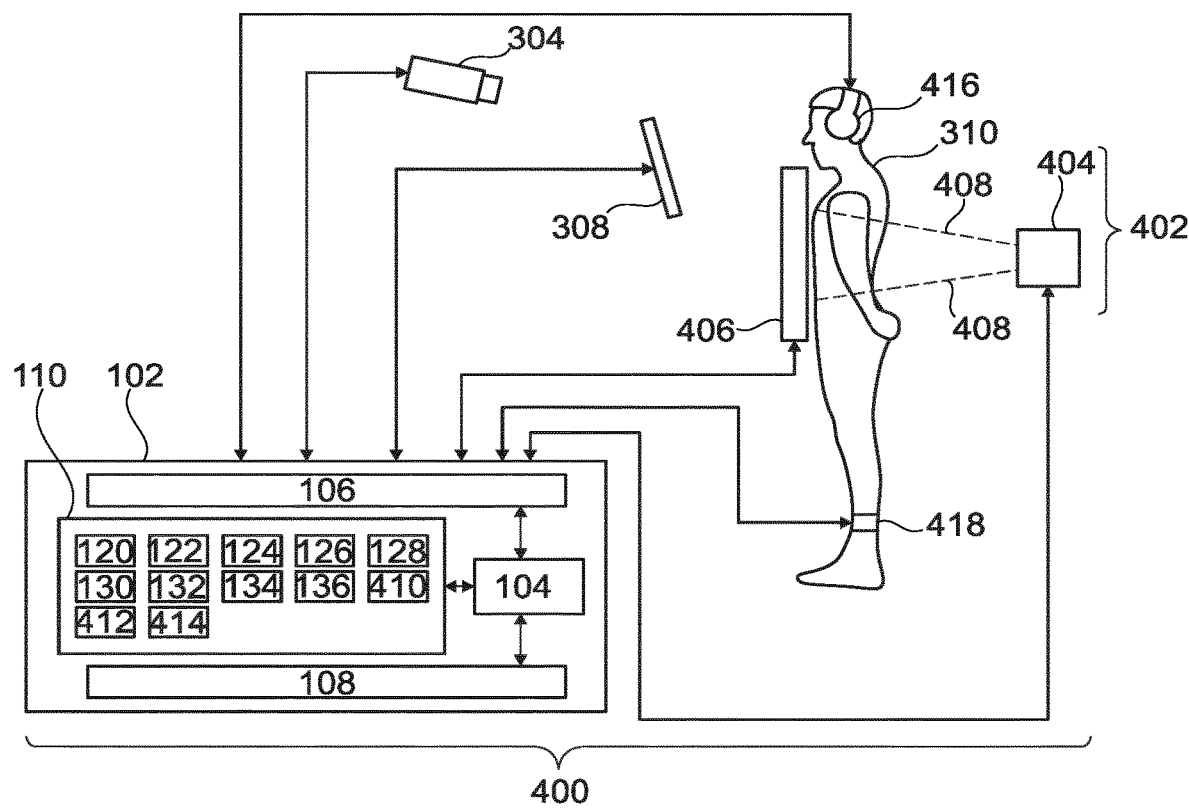
FIG. 4 illustrates a further example of a medical system.

FIG. 4 illustrates a further example of the medical system 400. The medical system 400 is similar to the medical systems 100 and 300 illustrated in FIGS. 1 and 3. In this instance the medical system 400 is shown as comprising a digital X-ray system 402. The digital X-ray system 402 is an example of a medical imaging system. The digital X-ray system 402 could for example be replaced by a digital fluoroscope system, a magnetic resonance imaging system, a computed tomography system, a positron emission tomography system or a single photon emission tomography system also.

The digital X-ray system 402 comprises an X-ray generator 404 and an X-ray detector 406. The dashed lines 408 indicate the path of X-rays. A subject 310 is shown as standing between the X-ray detector 406 and the X-ray generator 404. The subject 310 is attempting to position her or himself properly for an examination. A camera system 304 is shown again as being visible.

In this example there are three examples of three different types of user interfaces which may be used for providing one or more one-dimensional position indicators. There is a display 308 for providing visual feedback to the subject 310. The subject 310 is also shown as wearing headphones 416, which are able to provide an audio signal to the subject 310 which may be used as one or more one-dimensional position indicators. The headphones 416 are intended to be an example of one type of a user interface which could provide the audio signal to the subject. Other types of audio transducers, such as speakers, could be substituted for the headphones 416. The use of headphones 416 has the advantage that the position of the subject's head does not affect how the subject perceives the audio signal. With an external speaker, the subject's perception of the audio signal could change as the subject moves.

The subject 310 is also shown as wearing a haptic feedback system 418. The haptic feedback system 418 may for example vibrate with a different amplitude as a function of the one-dimensional value.

Various subjects may have different impairments. For example, if the subject 310 has trouble seeing then the headphones 416 and possibly the haptic feedback system 418 may be used. If however the subject 310 has difficulty hearing, then the use of the display 308 or the haptic feedback system 418 may be more appropriate. The configuration of the user interface can therefore be very flexible and configured for the needs of the individual subject 310.

The memory 110 is shown as optionally containing an additional image protocol selection 410. The memory 110 is further shown as containing an optional database 412. The database 412 may be queried using the image protocol selection 410 to retrieve a set of positioning instruction steps 414. The set of positioning instruction steps 414 may for example be used to provide instructions using the display 308, the headphones 416 and/or the haptic feedback system 418.

Figure 5:
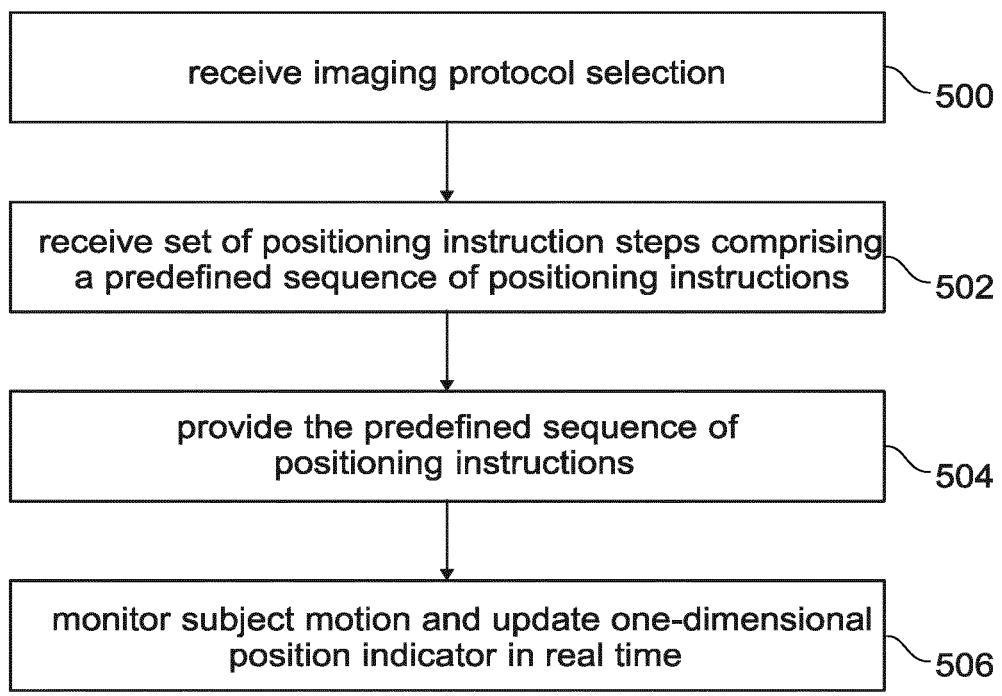
FIG. 5 shows a flow chart which illustrates a method of using the medical system of FIG. 1, FIG. 4, or FIG. 5.

FIG. 5 shows a flowchart which illustrates a further example of the method. The method starts with step 500. In step 500 an imaging protocol selection 410 is received. Next, in step 502, the imaging protocol selection 410 is used to query a database 412. In response to this query, the database retrieves and provides a set of positioning instruction steps 414. The set of positioning instruction steps 414 describe a predetermined sequence of positioning instructions. These predetermined positioning instructions may for example be provided using the display 308, the headphones 416 or the haptic feedback system 418.

The at least one of the sequence of positioning instruction steps 414 comprises the at least one set of predetermined coordinates 124. Next, in step 504, the predetermined sequence of positioning instructions is provided using the user interface 108, 308, 416, 418. Finally, in step 506, subject 310 motion is monitored during the providing the predetermined sequence of positioning instructions. The one-dimensional position indicator is provided or modified in real time for the at least one of the predetermined sequence of positioning instructions.

In case one does not make use of e.g. the features as described in the above flowchart of FIG. 5, when providing positioning guidance to subjects, the instructions may only work well for easy movements—e.g. (i) stand against the middle of the wall stand, (ii) put your hands behind your back—but fail for more complex movements that involve unusual body positions—e.g. (iii) curl your shoulders against the wall stand.

For example, to guide the patient on the proper position for a chest X-ray is quite complicated because there are many degrees of freedom just for the shoulders/spine positioning:

Shoulders horizontal level (left and right at same height), i.e. alignment along x axis
Shoulders forward rotation (left and right as close as possible to detector plate), i.e. alignment along z axis
Spine vertical alignment, i.e. alignment along y axis.

To guide the patient in 3 degrees of freedom with a visual is very challenging. First, the visualization will be in 3D, which is cognitively complicated for a majority of patients who are not used to navigate in such representations. Second, guiding the patient along these separate 3 axes implies that the patient has a sufficient body awareness in terms of spatial representation to decouple mentally the movement of their body along these axis separately Finally, in breaking down the movement into three steps, the adjustment the patient makes on the next step is likely to cause the requirement obtained in the previous step to be violated again. E.g. spinal alignment is likely to cause a slight backward movement of the shoulders, thereby violating the forward rotation requirement obtained in the previous step.

Some examples may therefore provide for a one-dimensional position indicator, such as a visualization where several degrees of freedom are combined (2D—>1D), giving a visual feedback to the patient that is intuitive to follow and provides simultaneous, rather than stepwise alignment of the body posture. The combination of multiple degrees of into a single one dimensional position indicator may be implemented in several different ways. In one example, a multi-dimensional movement (such as a two-dimensional or 2D movement) is combined simultaneously.

In other examples, the one-dimensional position indicator is configured to add the effects of additional degrees of freedom sequentially. For example, complicated motions may require a subject to position a body part using movement in multiple directions, stretch, twist, and/or to rotate the body part. As the subject achieves an intermediate position or pose, the objective function is altered to include additional terms representing additional constraints.

The use of multiple one-dimensional position indicators may be implemented in different ways. For example, multiple one-dimensional position indicators may be provided. In one example multiple one-dimensional position indicators are used to provide feedback on multiple positioning motions simultaneously. For example, a subject may move her or his shoulders with a great degree of independence. A one-dimensional position indicator may be provided for each shoulder. This is also true for the positioning of many different body parts.

In other examples, the multiple one-dimensional position indicators may be provided sequentially. As a portion of the subject is positioned properly an additional one-dimensional position indicator may be provided.

In some of these examples, stepwise instructions are first provided. If the patient or subject is not able to reach the correct position then a one-dimensional position indicator may be provided to assist the subject to achieve the correct position or posture.

Examples may comprise one or more elements of the following:
1. A target posture (desired subject posture 1100) that involves a set of movements (set of positioning instruction steps 414) to reach it from the patient natural posture.
2. An identification of the movements within the set of movements that are non-distinct for the patient. Non-distinct means that the patient is not able with a simple instruction on one of the movements to perform it without performing one of the other movements at the same time. This identification can be realized by e.g. pre-testing the guidance concept on a group of patients.
3. A joint representation of the instruction on the non-distinct movements, i.e. one target in the instruction (visual, audio, haptic) is reached only if the two (or more) non-distinct movements have been performed correctly.

Figure 6:
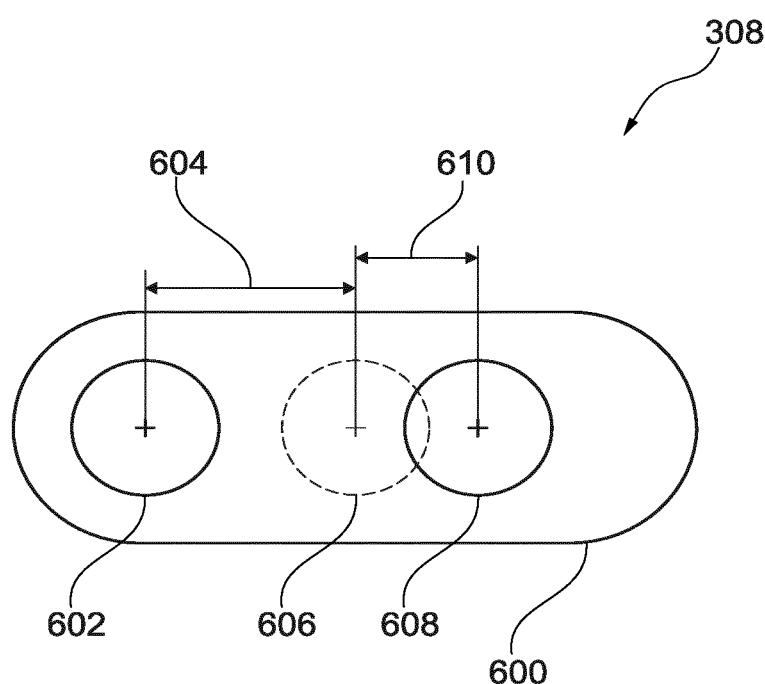
FIG. 6 show a view of a display with multiple one-dimensional position indicators.

FIG. 6 illustrates an example of a display which contains several different one-dimensional position indicators 600, 602, 608. The first position indicator is a first rotational one-dimensional position indicator 500 that is shown in the aligned position. The display 308 also shows two separate displacement one-dimensional position indicators 602, 608.

There is a first displacement one-dimensional position indicator 602 which shows the displacement of the object 602 from an alignment position 606. It can be seen that the first displacement one-dimensional position indicator 602 is a first displacement 604 away from the displacement one-dimensional alignment position 606. There is also a second displacement one-dimensional position indicator 608 that is a second displacement 610 away from the alignment position 606. The display 308 may be particularly useful when a subject tries to position multiple body parts. For example, the first displacement one-dimensional position indicator 602 could indicate the location of a first shoulder. The second displacement one-dimensional position indicator 608 could represent a second shoulder. When both shoulders are aligned properly, they overlap at the aligned position 606. As each shoulder is worse aligned, the first displacement 604 and the second displacement 610 increase.

The example in FIG. 6 resembles a spirit level or bubble level. in the way it potentially:
Demonstrates the correct posture/position
Provides feedback on the current posture/position versus the correct posture/position: there is a direct feedback loop showing with each movement whether the movement is bringing the posture closer or moving it further away from the correct posture.

Figure 7:
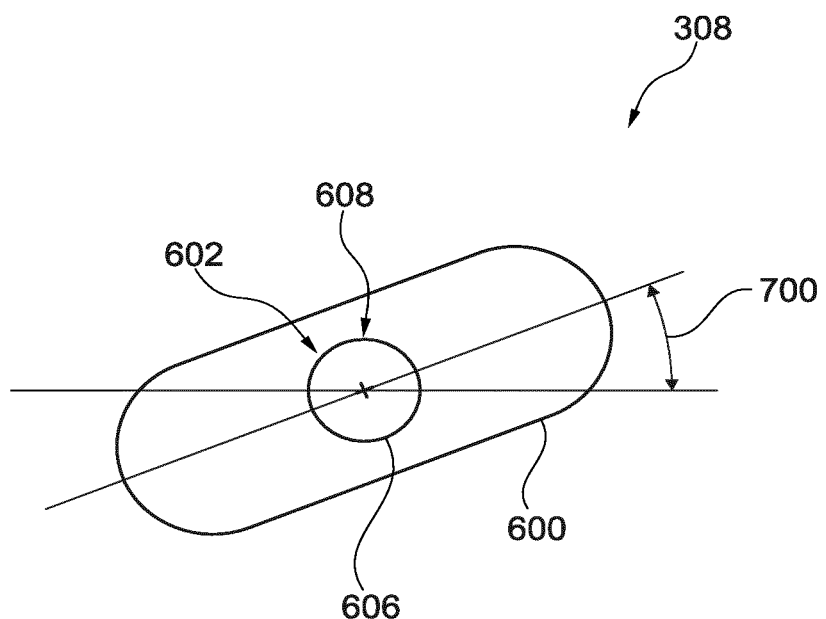
FIG. 7 show a further view of a display with multiple one-dimensional position indicators.

FIG. 7 shows a further view of the one-dimensional position indicators of FIG. 6. In this example both the first displacement one-dimensional position indicator 602 and the second displacement one-dimensional position indicator 608 are shown in the alignment position 606. However, the first rotational one-dimensional position indicator 600 has been rotated by an angle 700. The value of the angle 700 may be determined by the one-dimensional value. FIGS. 6 and 7 illustrate how three separate one-dimensional position indicators 600, 608, 602 can be shown on the same display 308. The angle 700 could for example be useful in providing feedback to the user about the alignment of her or his spine.

Figure 8:
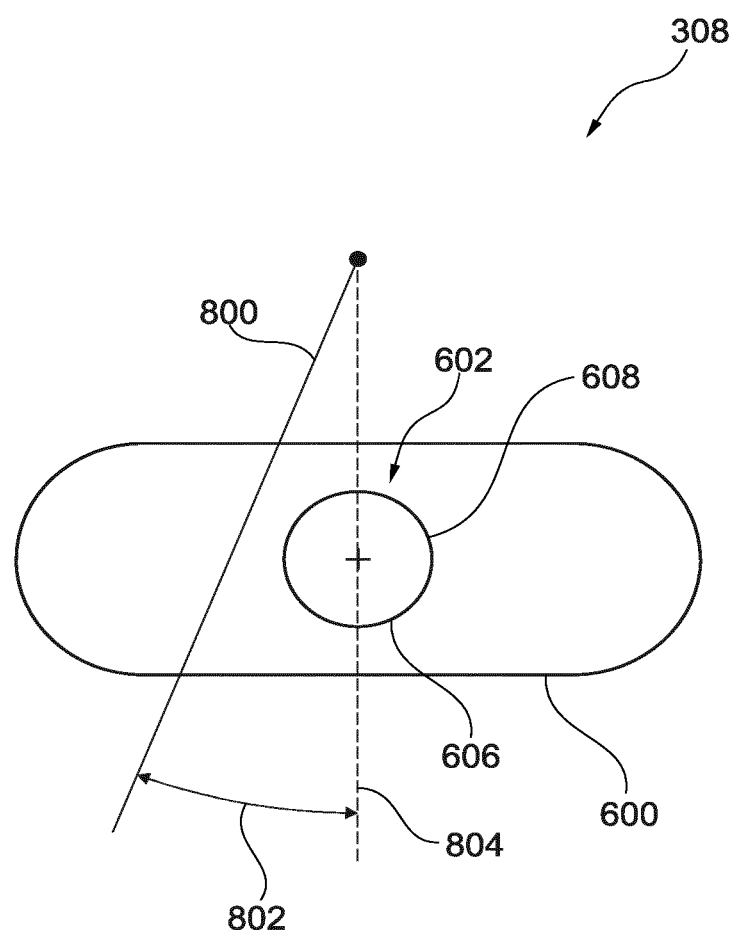
FIG. 8 show a further view of a display with multiple one-dimensional position indicators.

FIG. 8 shows how the display 308 of FIGS. 6 and 7 may be modified to add a fourth one-dimensional position indicator 800. In this example, there is a line 800 which represents a second rotational one-dimensional position indicator 800. This indicator 800 rotates at an angle 802 from an alignment position 804. FIG. 8 illustrates one way in which the amount of information provided to a subject may be increased.

The alignment of the spine is a straightforward axis alignment representation and can be represented in various ways using the examples of the rotational one-dimensional indicators illustrated in FIGS. 7 and 8.

FIGS. 6 through 8 shows how the spirit level visualization is used to provide guidance on three dimensions of body movement:
1. Horizontal alignment of the shoulders, i.e. alignment along x axis
2. Forward rotation of the shoulders, i.e. alignment along z axis
3. Vertical alignment of the spine, i.e. alignment along y axis through providing feedback on two dimensions, in a x-y plane representation:
    The movement of the black dot towards the left or the right of the center of the bar
    The tilting (700) of the level bar on the vertical axis
The movement of the shoulders (horizontal alignment and forward rotation) is combined into 1 dimension, leaving a very simple feedback visualization with either the black dot to the left or right of the center, indicating a misalignment of the shoulders, or the bar tilted, indicating a misalignment of the spine.

Through moving the shoulders, the patient will see the dot moving towards the center or away from it and can thereby find the right position of the shoulders without having to rely on knowledge of how to isolate movement of the shoulders forward or backward or horizontally.

For other movements that involve only one body part (e.g. one shoulder, one knee), the spirit level has only one black dot.

In this representation, the system can measure the degree of rotation forwards and horizontal and map it onto the length of the bar to determine where the black dot should be in relation to the center of the bar. For the spine, the system can measure how far the farthest point is from the straight line projected onto the spine and then map that onto a degree of rotation of the bar.

Other visualization than the spirit level can be implemented. As an example, in the case of the chest X-Ray positioning:
    Each shoulder is represented by a shape of which the size depends on the proper positioning. The closer to the ideal position, the smaller the shape.
    Haptic feedback such as vibration diminishes as the shoulder reaches the target position.
    Light signal turns from red to green as the shoulder reaches the target position.
    Sound from high pitch high frequency to a harmonious low bell ringing as the shoulder reaches the target position.
    And so forth Other embodiments in body positioning for scanning purposes include postures which may have three degrees of freedom. Especially postures that are difficult to attain when the subject has no physical training. Examples are:
    Postures where the hips need to be rotated as this will typically result in movement of the spine and the legs as well
    Postures where you need to hold your arm out to the side or the front, but the shoulder down and the back straight
    Movement of the ankle joint without moving the leg. As the ankle can make full rotation, it can be difficult to find the exact right position
    Movement of the wrist joint without moving the arm
    Having the fingers in a certain position, e.g. to make an X-ray of a finger in a position where it is covered by other fingers if the hand is held in a relaxed position, while holding the hand steady in the correct position In another embodiment, this invention can help execute physiotherapy exercises at home, when the patient is not guided by the physiotherapist.

There are two types of exercises:
    Holding of a certain posture, e.g. to stretch or to train muscles
    Repeating a certain movement For both, the invention can support the patient in executing the exercise: For holding a certain posture, the visualization can provide continuous feedback on whether the patient is still holding the correct position. For example, holding a plank position, it is important to
    have the hands below the shoulders: the shoulders can move backwards or forwards have a straight back bring the hips down so the back and legs are in a straight line For repeating a certain movement, the visualization can provide feedback on the extremes/endpoints of the movement, to make sure the movement is as effective as possible.

For example, rehabilitation exercises for the ankle include flexing the ankle while lying down and keeping the knee straight. This movement should be made until you feel discomfort. However, what would be described as discomfort can vary greatly among individuals. Using this invention, the physiotherapist can set a goal together with the patient that may either push the patient a bit past their level of discomfort or may restrain the patient a bit more than they would on their own. The right degree of flexion can be set to where the black dot in the visualization is exactly in the middle. This way, when the patient is at home, he/she can get visual feedback to let them know when to stop the movement and go back to the neutral position, while at the same time making sure they keep the right posture for the movement.

Keeping the right posture is a big problem in many jobs today: office workers sit in a chair all day and develop back, neck and shoulder complaints; movers, construction workers and other jobs where heavy lifting is involved may develop back problems.

Keeping the correct posture is difficult as during the day, your attention will drift away from your posture. The simple visualization presented here can serve as a trigger to refocus attention to your posture.

Besides, making sure you have the correct posture can also be very difficult. For many people, correcting their posture involves multiple degrees of freedom, involving:

the legs: knees bent in 90 degree angle, or standing straight on both legs the hips: rotated forward when sitting as well as standing back: straightening the lower back as well as the upper back shoulders: having the shoulders down and twisted backwards neck: usually involved moving the head backwards and the chin down When correcting posture, one will usually focus on one of these movements, e.g. straightening the lower back, but if the other movements are not taken into account, this may lead to a displacement of the complaints to a different part of the body.

Figure 9:
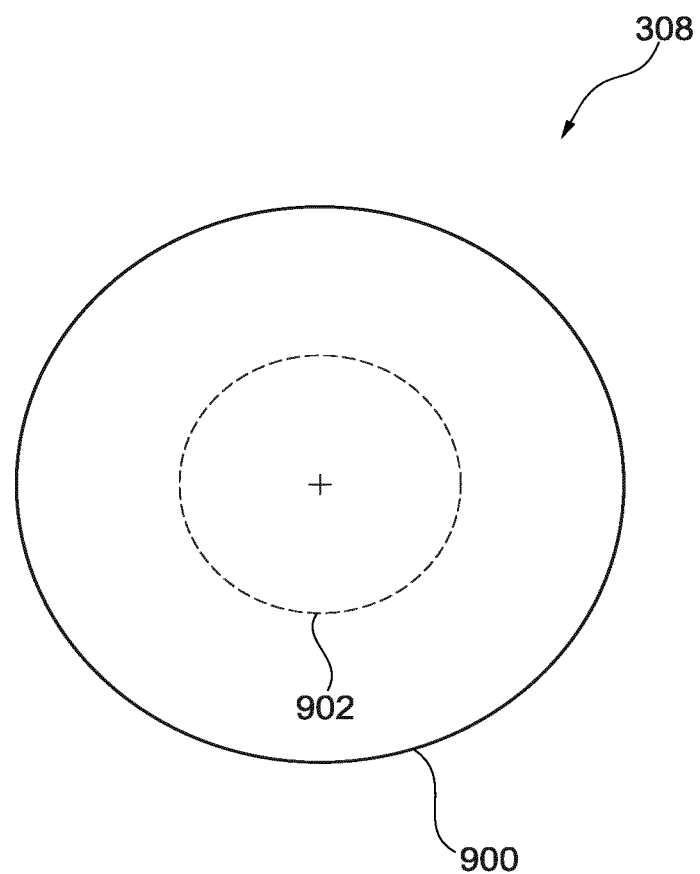
FIG. 9 show a view of a display with a one-dimensional position indicator.

FIG. 9 shows a further example of a display 308 that shows a size-based one-dimensional position indicator 900. The size of the one-dimensional position indicator 902 can change with the value of the one-dimensional value. When the one-dimensional position indicator 900 indicates that the position is aligned it may have the alignment size 902 indicated by the dashed circle. The previous examples have illustrated how a one-dimensional position indicator could be constructed for visual feedback.

Figure 10:
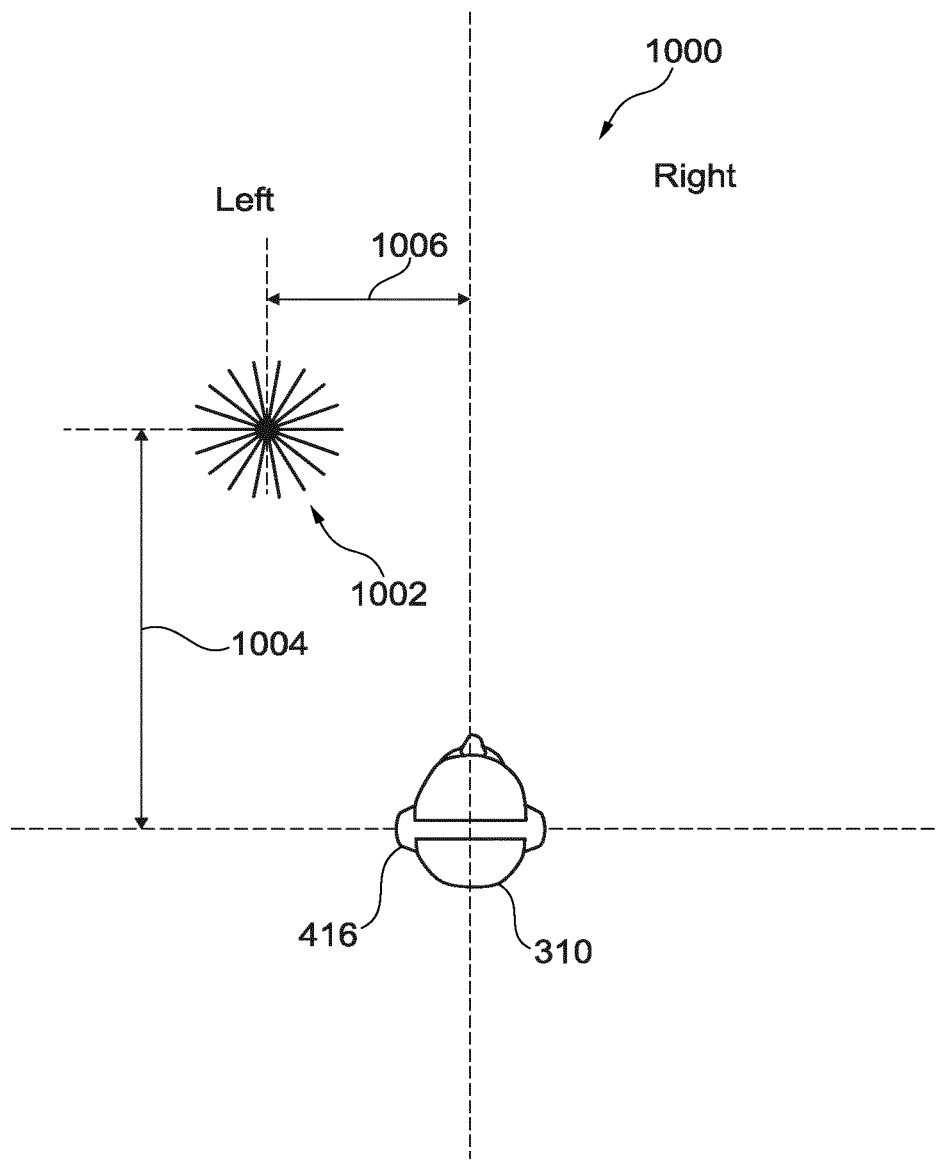
FIG. 10 illustrates multiple one-dimensional position indicators that a provided using a stereo acoustic field.

FIG. 10 illustrates one example of an acoustic user interface 1000. There is a subject 310 wearing headphones 416. By providing different sounds to the different ears a stereo acoustic image 1002 may be constructed. This stereo acoustic image 1002 may have a distance from the subject 1004 and a left-right position 1006. The distance 1004 and the position 1006 provide two different one-dimensional position indicators. This may, among other things for example, provide a person who is visually impaired the means to align two different body parts. The exact position of the stereo acoustic image 1002 may be controlled in different ways.

For example, varying the amplitude may give the appearance of it coming closer to the subject 310. Changing the balance of volume between the left and right may also be used for adjusting the left-right position 1006. However, various psychoacoustic models may also be used to better control this. For example, slight delays may be introduced between the sound provided to the left and right ears to better make a stereo acoustic image 1002.

Providing the stereo acoustic image 1002 is not the only way in which a one-dimensional position indicator can be provided on an audio basis. The pitch, timbre, volume and other properties may also be varied as a function of a one-dimensional value.

For many medical examinations the patient must adopt a certain position and a certain posture. For example, for an MR scan, the patient may need to put her hands above her head. For a knee examination, they may need to bend their knee. For a chest X-ray, the patient needs to put their hands on her back and curl her shoulder blades forward. Currently, there are experienced technicians who explain to the patient what to do and may gently push the patient into the right position and posture.

However, due to the rising costs of healthcare, and the trend to bring diagnostic imaging in delocalized health centers with less specialized staff, there is a push towards using less trained staff who may lack the knowledge, skills and experience to help patients adopt the right posture. Adopting the right posture however is critical to a good image quality and limiting the number of retakes. Within Philips, there are several research projects which prepare for a future in which medical imaging happens autonomously and in which no nurses or technicians of flesh-and-blood are present during an examination (Autonomous Imaging).

In general, even in the presence of a technician, it is wanted to make the examination faster. This is especially true for chest X-ray imaging, that sees an increasing demand due to the surge of lung-related diseases. In China, up to 600 chest X-ray examinations are performed on a single machine per day. Any mean to make the positioning of the patient faster is thus welcome.

Therefore, a system which instructs the patient on the posture to adopt and make the right positioning faster, more accurate and steadier is beneficial. Such instructions can be visual (e.g. 2D visuals, 3D visuals, animated visuals, video) and/or audible (e.g. spoken or abstract, compare to the sound warnings when parking a car).

As an example of a guidance concept, a system for chest X-rays based on short loops of 3D animation may be implemented. In such a loop, an animated human character (e.g. an avatar or 'virtual twin') shows the movement that is required to move from the patient's current posture into the required posture, together with audible instructions. Body parts and their movement may be emphasized through various visual means (e.g. arrows, color and lighting). The total posture change required is split up into manageable, understandable sub movements (e.g. a frontal chest x-ray is split up into (i) stand against the middle of the wall stand, (ii) put your hands behind your back, (iii) curl your shoulders against the wall stand). Each of these sub movements is explained through a looped 3D animation. The loop plays until the patient adopts the right posture, which is detected by using computer vision (e.g. a depth camera).

Figure 11:
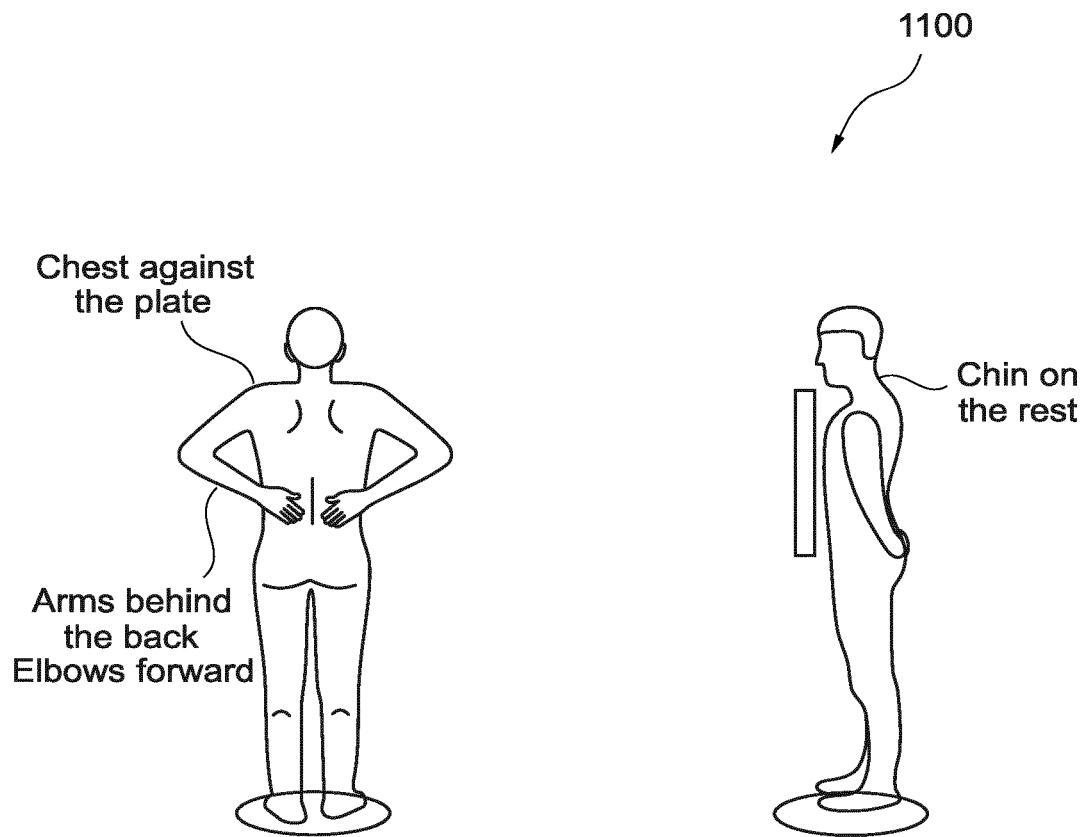
FIG. 11 show a depiction of a desired subject position for an x-ray examination.

FIG. 11 shows a desired subject position 1100 which may for example be displayed to a subject when an imaging protocol selection 410 is made.

Figure 12:
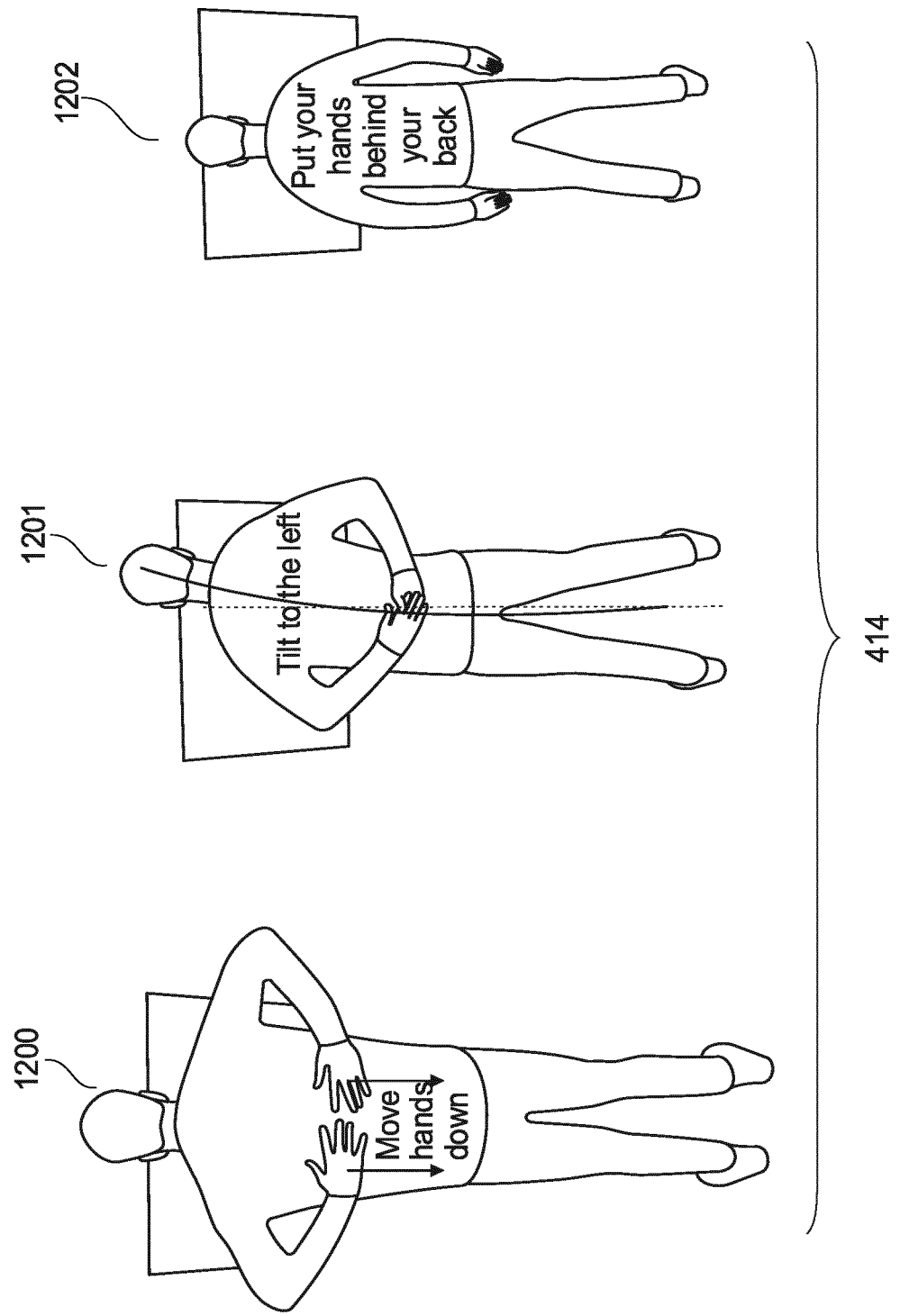
FIG. 12 shows three images which represent a set of sequential positioning steps.

FIG. 12 illustrates a set of positioning instruction steps 414. The set of positioning instruction steps 414 is shown as comprising machine instructions 1200, 1202, and 1204. In this example the complex movement to achieve the position 1100 may be chopped up into understandable chunks. Each of these pictures 1200, 1201, 1202 may be an animation loop. This may be done using real life video or with animations. For example, an animated 3D character could be adapted in real time to the actual position of the subject. The images 1200, 1201, and 1202 may for example be displayed in addition to the position indicators such as are displayed in FIGS. 6, 7, and 8.

FIGS. 11 and 12 illustrate how complex movement may be 'chopped' up into understandable chunks. Each of these three pictures is in fact an animation loop. Though this is real-life video, we imagine the person to be a 3D animated character of which the movements can be adapted in real time.

Figure 13:
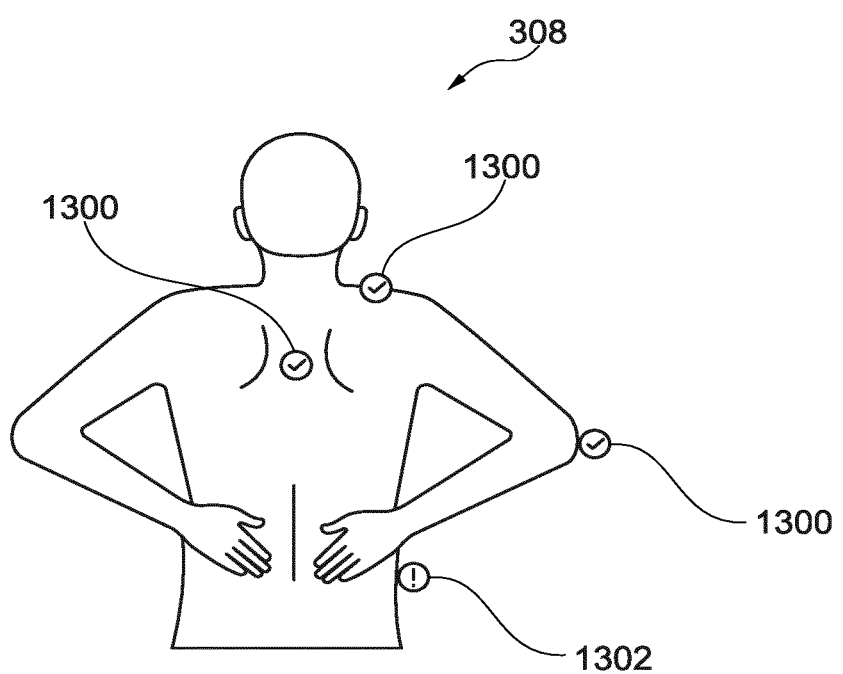
FIG. 13 illustrates the use of success indicators.

When a subject is positioning her or himself it may be difficult for the subject to maintain the position of body parts which are already positioned. FIG. 13 shows an additional display which may be added to a display 308, which shows an idealization of a subject with a number of success indicators 1300 and misaligned indicators 1302. As a subject successfully completes one of the positioning instructions 1200, 1202, or 1204 a success indicator 1300 may be displayed. As the camera is constantly monitoring the subject, if a body part or portion goes into misalignment this may be indicated to the subject by providing a misaligned indicator 1302 or the removal of a success indicator 1300.

The display illustrated in FIG. 13 may be augmented with one-dimensional position indicators such as are illustrated in FIGS. 6 through 9. In one example the misaligned indicators 1302 have their size changed, as is illustrated in FIG. 9, to indicate improved positioning. The misaligned indicators 1302 could start with an increased size which then shrinks as the current coordinates becomes aligned with the predetermined coordinates. When the current coordinates are aligned with the predetermined coordinates then the misaligned indicator changes into a success indicator 130.

Figure 14:
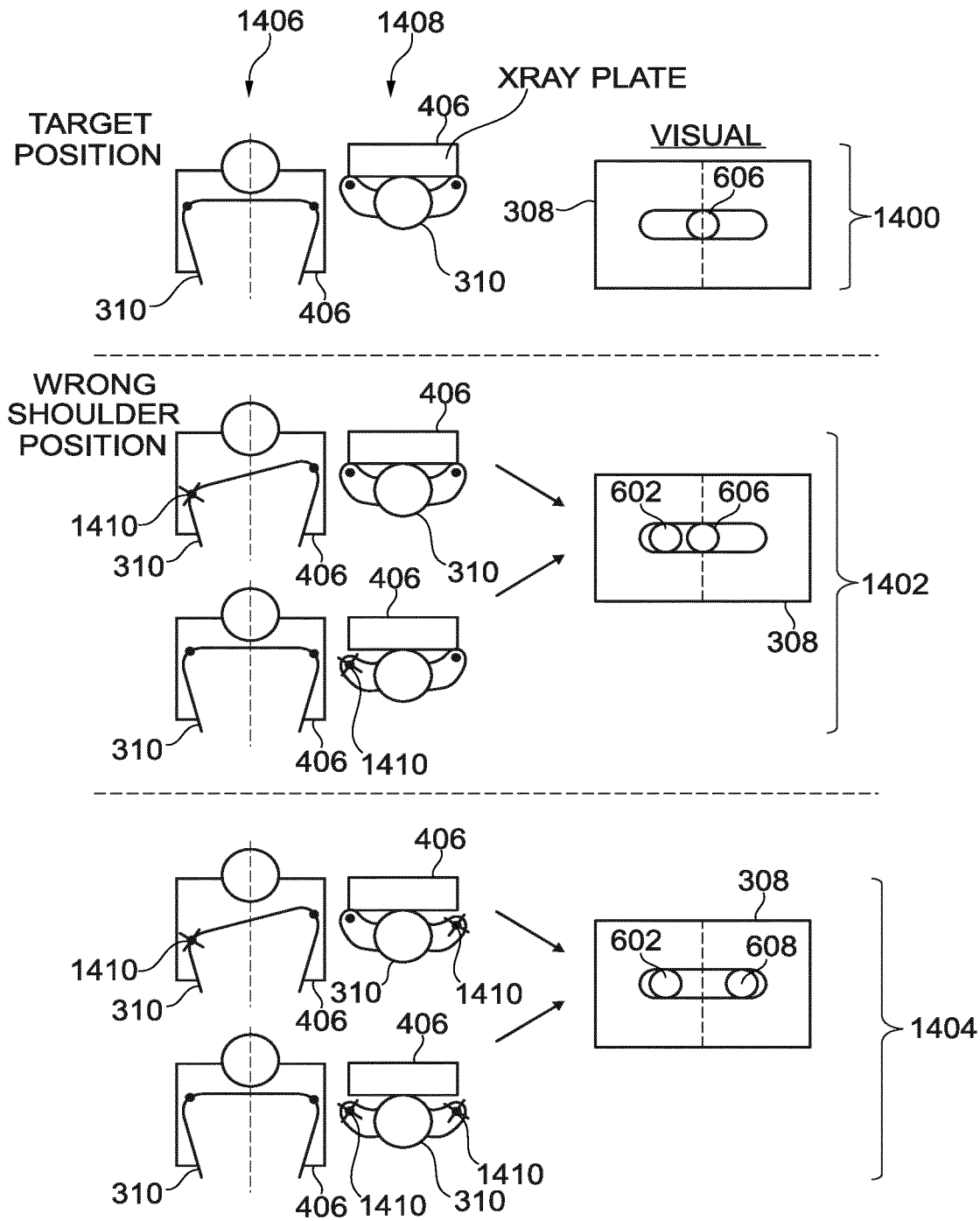
FIG. 14 illustrates the use of the one-dimensional position indicators of FIG. 6 through 8 for positioning two shoulders of a subject.

In FIG. 14 there are three different views of the display 308. The first one 1400 shows a first view of the display where the subject 310 has both shoulders aligned properly. The second display 308 shows a second view 1402 where one shoulder is misaligned. There is a third view of the display 308 labeled 1404, which shows two shoulders that are misaligned. The first column 1406 shows a back view of a subject 310 in front of an X-ray detector 406 as is illustrated in FIG. 4. Column 1408 shows a top view of the subject 310 in front of the same X-ray detector 406. In the first view 1400 both shoulders are aligned properly and the display 308 shows that both shoulders are aligned.

The second view 1402 of the display 308 shows that the left shoulder 1410 is misaligned. There are actually two possibilities which could lead to the display 1402. The shoulder 1410 could be either too low, as is illustrated in the two top images, or the shoulder could be the wrong distance from the X-ray detector 406. Both of these two possibilities are illustrated to the left of the second view 1402.

The third view 1404 of the display 308 shows both shoulders being misaligned. The various different possibilities could result in the same display. In the top the left shoulder is too low and the right shoulder is the wrong distance from the X-ray detector 406. Another possibility is illustrated in the lower portion, where both shoulders 1410, are the wrong distance from the X-ray detector 406. When the subject sees the displays 1402 or 1404, she or he will gradually move the shoulder in different positions and notice that when the shoulder is moved in a particular direction the indicators 602 or 608 move closer to the aligned position 606. The subject 310 can then position her or himself with minimal or no training.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

REFERENCE SIGNS LIST 100 medical system
102 computer system
104 computational system
106 hardware interface
108 user interface
110 memory
120 machine executable instructions
122 position identifying algorithm
124 at least one set of predetermined coordinates
126 current image
128 set of current coordinates for each of the at least one set of predetermined coordinates
130 positional difference
132 objective function
134 one-dimensional values
136 one-dimensional position indicators
200 repeatedly receive the current image from a camera system
202 receive the set of current coordinates for each of the at least one set of predetermined coordinates in response to inputting the current image into the position identifying algorithm
204 calculate a positional difference between the at least one set of predetermined coordinates and its set of current coordinates
206 calculate a one-dimensional value for each of the at least one set of predetermined coordinates by inputting the positional difference for each of the at least one set of predetermined coordinates into an objective function
208 provide a one-dimensional position indicator for each of and controlled by each one-dimensional value in real time using a user interface
300 medical instrument 302 diagnostic ultrasound system
304 camera system
306 ultrasound transducer
308 display
310 subject
312 subject support
314 one-dimensional position indicator
316 one-dimensional displacement
318 object
320 position of object when transducer is aligned
400 medical system
402 digital x-ray system
404 x-ray generator
406 x-ray detector
408 path of x-rays
410 imaging protocol selection
412 database
414 set of positioning instruction steps
416 headphones
418 haptic feedback system
500 receive an imaging protocol selection
502 retrieve a set of positioning instruction steps for positioning the subject by querying a database with the imaging protocol selection
504 provide the predefined sequence of positioning instructions using the user interface
506 monitor subject motion during providing the predefined sequence of positioning instructions
600 first rotational one-dimensional position indicator
602 first displacement one-dimensional position indicator
604 first displacement
606 alignment position
608 second displacement one-dimensional position indicator
610 second displacement
700 angle
800 second rotational one-dimensional position indicator
802 angle
804 alignment position
900 size one-dimensional position indicator
902 alignment size
1000 acoustic user interface
1002 stereo acoustic image
1004 distance from subject one-dimensional position indicator
1006 left/right position one-dimensional position indicator
1100 desired subject position
1200 positioning instructions
1202 positioning instructions
1204 positioning instructions
1300 success indicator
1302 misaligned indicator
1400 first view of display (subject aligned)
1402 second view of display (one shoulder mis-aligned)
1404 third view of display (two shoulders mis-aligned)
1406 back view of subject
1408 top view of subject
1410 mis-aligned shoulder

The invention claimed is:

1. A medical system comprising:
a memory configured to store machine executable instructions, at least one set of predetermined coordinates, and a position identifying algorithm, wherein the position identifying algorithm is configured to output a set of current coordinates for each of the at least one set of predetermined coordinates in response to receiving a current image descriptive of an object, wherein the at least one set of predetermined coordinates are anatomical locations, and wherein the object is a subject;
a camera system;
a user interface comprising a display;
a medical imaging system, wherein the medical imaging system is at least one of the following: an x-ray system, a digital fluoroscope, a magnetic resonance imaging system, a diagnostic ultrasound system, a computed tomography system, a positron emission tomography system, and a single photon emission tomography system, wherein each of the at least one set of predetermined coordinates defines a three-dimensional position and orientation of a body part of the subject relative to an imaging zone of the medical imaging system; and
a computational system configured to control the medical system, wherein execution of the machine executable instructions causes the computational system to repeatedly receive the current image from the camera system, wherein execution of the machine executable instructions further causes the computational system to perform the following for the current image:
receive the set of current coordinates for each of the at least one set of predetermined coordinates in response to inputting the current image into the position identifying algorithm;
calculate a positional difference between the at least one set of predetermined coordinates and its set of current coordinates;
calculate a one-dimensional value for each of the at least one set of predetermined coordinates by inputting the positional difference for each of the at least one set of predetermined coordinates into an objective function; and
provide a one-dimensional position indicator for each of and controlled by each one-dimensional value in real time using the user interface.

2. The medical system of claim 1, wherein the one-dimensional position indicator for each of the at least one set of predetermined coordinates is adapted to provide real time feedback on the alignment of the object to the at least one set of predetermined object coordinates.

3. The medical system of claim 1, wherein execution of the machine executable instructions further causes the computational system to:
receive an imaging protocol selection;
retrieve a set of positioning instruction steps for positioning the subject by querying a database with the imaging protocol selection, wherein the set of positioning instructions steps describe a predetermined sequence of positioning instructions, wherein at least one of the sequence of positioning instruction steps comprises the at least one set of predetermined coordinates;
provide the predefined sequence of positioning instructions using the user interface; and
monitor subject motion during providing the predefined sequence of positioning instructions, wherein the one-dimensional position indicator is provided in real time for the at least one of the predefined sequence of positioning instructions, wherein the one-dimensional position indicator is preferably provided in real time after the subject motion is descriptive of a failure to successfully complete the at least one of the predefined sequence of positioning instructions.

4. The medical system of claim 3, wherein execution of the machine executable instructions further causes the computational system to:
provide a success indicator indicating positioning after each of the predefined sequence of positioning instructions if the set of current coordinates satisfy a predefined criterion; and
remove a success indicator if the set of current coordinates no longer satisfy the predefined criterion.

5. The medical system of claim 1, wherein the user interface is configured to provide at least one of the one-dimensional position indicator for each of the at least one set of predetermined coordinates as a haptic signal.

6. The medical system of claim 1, wherein the user interface is configured to provide at least one of the one-dimensional position indicator for each of the at least one set of predetermined coordinates as an audio signal.

7. The medical system of claim 6, wherein the audio signal comprises at least one of the following: an amplitude change, a pitch change, a timbre change, or a change in a stereo audio location.

8. The medical system of claim 1, wherein the user interface is configured to provide at least one of the one-dimensional position indicator for each of the at least one set of predetermined coordinates as a visual position indicator on a display, wherein the visual position indicator is at least one of the following: an object location along a predetermined path, a rotational position, an object size, or a color change.

9. The medical system of claim 1, wherein the position identifying algorithm is configured to output the set of current coordinates using at least one of the following:
a template based matching algorithm;
a pictorial structure model with a joint likelihood maximization algorithm;
probabilistic boosting tree algorithm;
a trained neural network; or
parameterized deformable model.

10. A method of operating a medical system, wherein the method comprises repeatedly receiving a current image from a camera system, wherein the method further comprises performing the following for the current image:
receiving a set of current coordinates for each of the at least one set of predetermined coordinates in response to inputting the current image into a position identifying algorithm, wherein the position identifying algorithm is configured for outputting the set of current coordinates for each of the at least one set of predetermined coordinates in response to receiving a current image descriptive of an object;
calculating a positional difference between the at least one set of predetermined coordinates and its set of current coordinates;
calculating a one-dimensional value for each of the at least one set of predetermined coordinates by inputting the positional difference for each of the at least one set of predetermined coordinates into an objective function; and
providing a one-dimensional position indicator for each of and controlled by each one-dimensional value in real time using a user interface that comprises a display,
obtaining images with a medical imaging system, wherein the medical imaging system is at least one of the following: an x-ray system, a digital fluoroscope, a magnetic resonance imaging system, a diagnostic ultrasound system, a computed tomography system, a positron emission tomography system, or a single photon emission tomography system, wherein each of the at least one set of predetermined coordinates defines a three-dimensional position and orientation of a body part of the subject relative to an imaging zone of the medical imaging system.

11. The method of claim 10, further comprising:
receiving an imaging protocol selection;
retrieving a set of positioning instruction steps for positioning the subject by querying a database with the imaging protocol selection, wherein the set of positioning instructions steps describe a predetermined sequence of positioning instructions, wherein at least one of the sequence of positioning instruction steps comprises the at least one set of predetermined coordinates;
providing the predefined sequence of positioning instructions using the user interface; and
monitoring subject motion during providing the predefined sequence of positioning instructions, wherein the one-dimensional position indicator is provided in real time for the at least one of the predefined sequence of positioning instructions, wherein the one-dimensional position indicator is provided in real time after the subject motion is descriptive of a failure to successfully complete the at least one of the predefined sequence of positioning instructions.

12. The method of claim 11, further comprising:
providing a success indicator indicating positioning after each of the predefined sequence of positioning instructions if the set of current coordinates satisfy a predefined criterion; and
removing a success indicator if the set of current coordinates no longer satisfy the predefined criterion.

13. A computer program comprising machine executable instructions for execution by a computational system controlling a medical system, wherein the computer program further comprises a position identifying algorithm, wherein the position identifying algorithm is configured to output a set of current coordinates for each of the at least one set of predetermined coordinates in response to receiving a current image descriptive of an object, wherein execution of the machine executable instructions causes the computational system to repeatedly receive the current image from a camera system, wherein execution of the machine executable instructions further causes the computational system to perform the following for the current image:
receive the set of current coordinates for each of the at least one set of predetermined coordinates in response to inputting the current image into the position identifying algorithm;
calculate a positional difference between the at least one set of predetermined coordinates and its set of current coordinates;
calculate a one-dimensional value for each of the at least one set of predetermined coordinates by inputting the positional difference for each of the at least one set of predetermined coordinates into an objective function; and
provide a one-dimensional position indicator for each of and controlled by each one-dimensional value in real time using a user interface that comprises a display,
obtaining images with a medical imaging system, wherein the medical imaging system is at least one of the following: an x-ray system, a digital fluoroscope, a magnetic resonance imaging system, a diagnostic ultrasound system, a computed tomography system, a positron emission tomography system, or a single photon emission tomography system, wherein each of the at least one set of predetermined coordinates defines a three-dimensional position and orientation of a body part of the subject relative to an imaging zone of the medical imaging system.

* * * * *